US009863006B2

(12) United States Patent
Dobbelaer et al.

(10) Patent No.: US 9,863,006 B2
(45) Date of Patent: Jan. 9, 2018

(54) SELECTIVE LYSIS OF CELLS BY IONIC SURFACTANTS

(75) Inventors: Irene Dobbelaer, Esch (NL); Sieglinde Neerken, Eindhoven (NL); Paul Van De Wiel, Eindhoven (NL); Bart Van Meerbergen, Sint-Job-in-'t-Goor (BE); Roel Penterman, Tisselt (BE)

(73) Assignee: Biocartis NV, Mechelen (BE)

( * ) Notice: Subject to any disclaimer, the term of this patent is extended or adjusted under 35 U.S.C. 154(b) by 335 days.

(21) Appl. No.: 14/118,570

(22) PCT Filed: Apr. 30, 2012

(86) PCT No.: PCT/EP2012/057897
§ 371 (c)(1),
(2), (4) Date: Nov. 19, 2013

(87) PCT Pub. No.: WO2012/168003
PCT Pub. Date: Dec. 13, 2012

(65) Prior Publication Data
US 2014/0087361 A1 Mar. 27, 2014

(30) Foreign Application Priority Data
Jun. 6, 2011 (EP) .................................... 11305692

(51) Int. Cl.
*C12Q 1/68* (2006.01)
*C12Q 1/04* (2006.01)
(52) U.S. Cl.
CPC ............... *C12Q 1/689* (2013.01); *C12Q 1/04* (2013.01)
(58) Field of Classification Search
None
See application file for complete search history.

(56) References Cited

U.S. PATENT DOCUMENTS

| | | | | |
|---|---|---|---|---|
| 5,364,763 | A | 11/1994 | Kacian | 435/7.32 |
| 6,027,750 | A | 2/2000 | Gautsch et al. | 424/489 |
| 6,803,208 | B2 | 10/2004 | Seaver et al. | 435/34 |
| 2010/0129858 | A1 | 5/2010 | Walsh et al. | 435/34 |
| 2010/0143878 | A1* | 6/2010 | Olson | C12N 1/06 435/2 |
| 2011/0076706 | A1* | 3/2011 | Fleming | C12Q 1/008 435/8 |
| 2013/0171615 | A1 | 7/2013 | Van Meerbergen et al. | 435/2 |

FOREIGN PATENT DOCUMENTS

| | | | | |
|---|---|---|---|---|
| EP | 0 285 439 A2 | 10/1988 | | C12Q 1/68 |
| JP | H09-168399 A | 6/1997 | | C12N 15/09 |
| JP | 2003-500674 A | 1/2003 | | B01J 19/00 |
| WO | WO 99/16869 | 4/1999 | | C12N 15/10 |
| WO | WO 00/72970 | 12/2000 | | B01L 3/00 |
| WO | WO 2009/135048 | 11/2009 | | C21N 15/10 |
| WO | WO 2010/062351 A1 | 6/2010 | | G01N 21/65 |
| WO | WO 2010/062356 A1 | 6/2010 | | G01N 21/65 |
| WO | WO 2011/070507 | 6/2011 | | C12Q 1/68 |

OTHER PUBLICATIONS

Zierdt, "Blood-Lysing Solution Nontoxic to Pathogenic Bacteria," Journal of Clinical Microbiology, vol. 15, No. 1, Jan. 1982, pp. 172-174.
Horz et al., "New methods for selective isolation of bacterial DNA from human clinical specimens," Anaerobe, London, United Kingdom, vol. 16, No. 1, Feb. 1, 2010, pp. 47-53.
Macfarlane et al., "Isolating RNA from whole blood—the dawn of RNA-based diagnosis?," Product Review, 1993 Nature Publishing Group, Nature, vol. 362, No. 6416, Mar. 11, 1993, pp. 186-188.
Heerklotz, "Interactions of surfacants with lipid membranes," Quarterly Reviews of Biophysics 41, Leslie Dan Faculty of Pharmacy, Toronto, ON, Canada, 2008, pp. 205-264.
International Search Report for International Application No. PCT/EP2012/057897, dated Oct. 15, 2012.
Notice of Rejection in corresponding Japanese Patent Application No. 2014-513963 dated Dec. 8, 2015 (English-translation provided).
"Eukaryotic cell," *Dictionary of Biology*, 4th ed., 3rd print, p. 667, Iwanami Shoten, Apr. 1997. <see relevance at p. 7 of English translation of Japanese Notice of Rejection (dated Dec. 8, 2015) for JP 2014-51393>.
"Micro-organism," *Dictionary of Biology*, 4th ed., 3rd print, p. 1151, Iwanami Shoten, Apr. 1997. <see relevance at p. 7 of English translation of Japanese Notice of Rejection (dated Dec. 8, 2015) for JP 2014-513963>.

* cited by examiner

*Primary Examiner* — Blaine Lankford
(74) *Attorney, Agent, or Firm* — Kusner & Jaffe

(57) ABSTRACT

The present invention discloses methods, kits-of-parts, and devices for the selective lysis of eukaryotic cells in a sample comprising micro-organisms such as bacteria unicellular fungi. The selective lysis is obtained by incubating the sample in an ionic surfactant under alkaline conditions.

10 Claims, 2 Drawing Sheets

SELECTIVE LYSIS OF CELLS BY IONIC SURFACTANTS

FIELD OF THE INVENTION

The present invention relates to the lysis of eukaryotic cells, in particular to the lysis of animal cells, such as blood cells. The present invention further relates to the detection of a small number of micro-organisms such as bacteria or fungi in samples containing a large number of other cells.

BACKGROUND OF THE INVENTION

Molecular diagnostics aims at the rapid detection of minute amounts of pathogens (typically bacteria) in samples such as blood. However, blood is a complex matrix and comprises white blood cells (leukocytes) for the adaptive immune system, red blood cells (erythrocytes) for oxygen transport, and platelets (thrombocytes) for wound healing. This composition complicates the direct detection of pathogens in samples such as whole blood, which contain a high amount of cellular material.

Classical detection methods comprise the growth of bacteria on selective media and/or media containing indicators. Typically such assays require a cultivation step of at least 1 or 2 days before identification of the bacteria can take place.

For PCR based methods the amount of bacteria in a fresh blood sample is theoretically high enough to be detected without further cultivation of the bacteria present within such sample. However, to allow an early detection of minute amounts of bacteria, large volumes of blood are required. The high amount of DNA in especially white blood cells dramatically increases the background in DNA based detection methods. Also the presence of heme from hemoglobin strongly decreases the activity of DNA polymerase. A microliter of human blood contains about 4,000 to 11,000 white blood cells and about 150,000 to 400,000 platelets. The concentration of DNA in blood is between 30 and 60 µg/ml. It is extremely challenging to detect the presence of about 10 to 100,000 of a bacterial species in a volume of 10 ml of whole blood.

The high amounts of DNA of the white blood cells may give rise to non relevant PCR products, or may scavenge the primers designed for the detection of bacterial DNA. This necessitates a thorough DNA purification and separation of eukaryotic DNA before the bacterial DNA can be detected via PCR or other methods.

Apart from interfering with the PCR reaction itself, the amount of mammalian DNA increases the viscosity of a sample. In addition, proteins and membranes from the lysed mammalian cells form complexes which prevent the filtration of a sample. This is particularly a problem for miniaturized devices. Further dilution of the large sample volume results in unacceptable long manipulation steps.

For the above reasons, methods to remove human DNA from a blood sample are accordingly required.

Methods to specifically assay bacterial DNA in the presence of mammalian DNA are known. Looxters™ from the company SIRSLab uses a method to enrich methylated DNA from a sample. As bacterial DNA is strongly methylated, this approach results in an enrichment of bacterial DNA. Molysis™ from the company Molzym, uses chaotropic agents and detergents to lyse selectively mammalian cells. This lysis step is followed by a digest with a DNAse which is not affected by this chaotropic agent/detergent. Alternative approaches such as commercialized by Roche (Septifast™) rely on PCR primer pairs which are specifically designed to prevent aspecific binding to human DNA and amplification of human DNA.

U.S. Pat. No. 6,803,208 describes a method wherein a highly diluted suspension of blood platelets doped with bacteria is lysed at 37° C. for 15 minutes, whereafter it is possible to filter a small amount of the lysed sample over a 0.4 µm filter for visual inspection of the bacteria which are retained on the filter. This method however does not allow to process large volumes of sample at ambient temperatures.

The non-published international patent application PCT/IB2010/055628 by Koninklijke Philips Electronics N.V. discloses a method for selective lysis of eukaryotic cells within a sample containing or suspected to contain micro-organisms, wherein a non-ionic detergent such as Triton X-100 (polyethylene glycol p-(1,1,3,3-tetramethylbutyl)-phenyl ether) and a buffer is added to a sample comprising eukaryotic cells to obtain a solution having a pH value of at least 9.5, and incubating said solution for a time period sufficiently long enough to lyse the eukaryotic cells. This method permits processing of blood samples having a volume of 5 ml by lysing the white and red blood cells in the sample, degrading the blood cell DNA while pathogenic micro-organisms remain intact, and can subsequently be enriched by centrifugation or filtration.

In his article "Interactions of surfactants with lipid membranes" (Quarterly Reviews of Biophysics 41 (2008), pages 205-264), H. Heerklotz discusses the hypothetical molecular mechanism of selective lysis of mammalian cells, and hypothesizes that said selective lysis depends on different steps. First, the surfactant ensures lysis of the white and red blood cells. In order to achieve this, the surfactant needs to be inserted in the outer layer of the cell membrane. In a second step, the surfactant will perform a so-called flip-flop and is transferred to the inner layer of the cell membrane. Once a sufficient amount of surfactant is present in the inner cell membrane and the outer cell membrane, the cell will be lysed. Non-ionic surfactants such as Triton X-100 were found to be well suited for cell lysis as they perform above-mentioned steps within a time frame of several hundred milliseconds. In contrast, SDS requires 10 to 30 s for its insertion into PC vesicles. In addition, it is reported that surfactants with larger or charged head groups may require hours or days to cross the membrane, as was shown for SDS at room temperature.

This hypothesis may explain why ionic surfactants are not suitable for obtaining fast lysis of mammalian cells as has been described in scientific literature (see Heerklotz, H.). Surfactants comprising a large, bulky or charged hydrophilic group such as Tween®, ionic surfactants and Tritons having a long PEG chain are slow at the flip-flop movement and thus not suitable to obtain rapid cell lysis. In addition, surfactants having a very hydrophobic character such as Brij® 35 or Triton X-45 will encounter difficulties in their initial insertion into the cell membrane. Ionic surfactants are considered not suitable for obtaining fast lysis of mammalian cells, because their charged hydrophilic group cannot perform the flip-flop transfer easily due to the presence of the charged hydrophilic group which has to pass the lipophilic membrane.

In contrast to the scientific knowledge, it has surprisingly been found that an ionic surfactant can be utilized for selective lysis of white and red blood cells while keeping microbial pathogens intact when said ionic surfactant is used in combination with high pH. Thus, in a first aspect, the present invention provides a method for selective lysis of eukaryotic cells within a sample containing or suspected to contain micro-organisms. In a second aspect, the present invention provides a kit-of-parts for performing the method for selective lysis of eukaryotic cells within a sample containing or suspected to contain micro-organisms. In a further aspect, the present invention provides a device for detecting micro-organisms in a sample containing eukaryotic cells.

SUMMARY OF THE INVENTION

Particular and preferred aspects of the invention are set out in the accompanying independent and dependent claims. Features from the dependent claims may be combined with features of the independent claims and with features of other dependent claims as appropriate and not merely as explicitly set out in the claims.

One aspect of the invention relates to a method for the selective lysis of eukaryotic cells, in particular animal cells, within a sample containing or suspected to contain micro-organisms. This method comprises the steps of providing a sample with eukaryotic cells, in particular animal cells, containing or suspected to contain a micro-organism, adding a buffer having a pH of about 9.0 or more, preferably a pH of about 9.5 or more and an ionic surfactant to the sample to obtain a solution having a pH of about 9.0 or more, preferably a pH of about 9.5 or more, and incubating the solution for a time period sufficiently long enough to lyse the eukaryotic cells, in particular animal cells.

In particular embodiments, the sample is a blood sample, such as for example whole blood. Preferably, the sample is a sample of vertebrate, more preferably of a mammal, in particular a domestic animal working animal or farm animal, and most preferably a sample of a human being.

In other particular embodiments the micro-organisms are bacteria and/or unicellular fungi. The method of the present invention may also be suitable for detecting unicellular eukaryotic pathogens such as flagellated protozoan or apicomplexan parasites.

According to particular embodiments, the ratio between the volume of added surfactant and added buffer and the volume of sample is between 2/1 and 1/10.

In particular embodiments, the alkaline buffer as used herein has a pKa value of above 9. Examples hereof are borate, carbonate, CAPS(N-cyclohexyl-3-aminopropanesulfonic), CAPSO (3-(cyclohexylamino)-2-hydroxy-1-propanesulfonic acid), CHES (2-(N-cyclohexylamino)ethane sulfonic acid), pyrophosphate and ethanolamine. A particular example is sodium carbonate.

In particular embodiments, the method further comprises the step of filtering the incubated solution on a filter with a pore size which retains micro-organisms on the filter, such as a filter with a pore size of less than 0.5 µm.

In particular embodiments, the method further comprises the step of adding after the selective lysis an acid or acidic buffer to obtain a pH between about 7 and 8 in the lysed solution, "a neutralization step".

In particular embodiments, the methods as described above are followed by lysis of the micro-organisms present in or suspected to be present in the sample.

Another aspect of the present invention relates to a kit-of-parts for performing the method described herein above. The kit comprises at least the alkaline buffer and the ionic surfactant. In preferred embodiments, the kit comprises a mixture of the alkaline buffer and the ionic surfactant in a fixed ratio. In an alternative embodiment, the kit comprises individual vials for the alkaline buffer having a pH of about 9.0 or more, preferably a pH of about 9.5 or more, and for the ionic surfactant such that the user can combine said alkaline buffer and said ionic surfactant in a desired ratio.

The kit-of-part may further comprise an acid or an acidic buffer in a particular embodiment for adjusting the pH of the solution to value of between about 7 and 8 after the alkaline lysis of the eukaryotic cells within the samples occurred. In yet another or additional embodiment, the kit may comprise a lysis buffer for lysing the microorganisms after they have been enriched, and for releasing the microorganism's DNA.

In particular embodiments, the kit-of-parts comprises at least one means for obtaining, processing and/or storing a sample or any solution that is generated or obtained during the processing of the sample.

In a further or additional embodiment, the kit-of-parts comprises at least one means for filtering the incubated solution. Said means may for example be a filter having a pore-size which retains the micro-organisms on the filter. The filter may have a pore size of less than 0.5 µm. The filter may be present in or part of a cartridge.

Another aspect of the present invention relates to a device (1) for the detection of micro-organisms in sample, comprising: a lysis chamber (2) for accepting a sample fluid with a volume between 1 and 20 ml, a reservoir (3) comprising an alkaline buffer with a pH of about 9.0 or more, preferably a pH of about 9.5 or more, and comprising an ionic surfactant, or a reservoir comprising an alkaline buffer (31) with a pH of about 9.0 or more, preferably a pH of about 9.5 or more, a reservoir comprising an ionic surfactant (32), connected to the lysis chamber, a filter (4) connected to the lysis chamber for filtering the sample after lysis, the filter having a pore size which retains bacteria on the filter, and a detection chamber (5) for assaying the presence of DNA.

Herein the alkaline buffer has typically a pKa above 9.0 and the ionic surfactant is typically sodium dodecyl sulfate.

Methods according to the present invention allow a selective lysis of white and red blood cells in a sample while bacteria and fungi remain intact (either dead or alive).

Methods according to the present invention make it possible to process a sample without substantially diluting such sample, and consequently allow to process larger volumes of sample. In addition, there is no need for enzymatic degradation of DNA by e.g. DNase, making this method less complex compared to methods known in the prior art.

Methods as described in the present invention result in lysed samples with a low viscosity and a minimum of aggregates, which makes it possible to filter the lysed sample over a filter which retains bacteria. Further processing of the bacteria on such filter can proceed with volumes between about 100-500 µl, which makes it possible to process large sample volumes for subsequent procedures and to perform the required manipulations, such as neutralization and washing, fully automated in an integrated cartridge.

The above and other characteristics, features and advantages of the present invention will become apparent from the following detailed description, taken in conjunction with the accompanying drawings, which illustrate, by way of example, the principles of the invention. This description is given for the sake of example only, without limiting the scope of the invention. The reference figures quoted below refer to the attached drawings.

Figure 1:
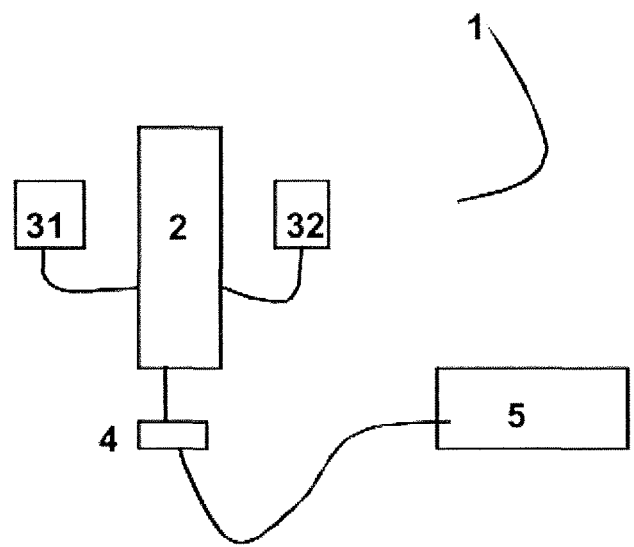
FIG. 1 shows a schematic overview of an embodiment of a device for performing a selective lysis as described in embodiments of the present invention.

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g. "a" or "an", "the"", this includes a plural of that noun unless something else is specifically stated.

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The following terms or definitions are provided solely to aid in the understanding of the invention. These definitions should not be construed to have a scope less than understood by a person of ordinary skill in the art.

DETAILED DESCRIPTION OF THE EMBODIMENTS

"Blood cells" in the context of the present invention relates to mammalian cells present in blood and includes red blood cells (erythrocytes), white blood cells (leukocytes) and blood platelets (thrombocytes).

"Whole blood" in the context of the present invention relates to unprocessed blood comprising blood plasma and cells, potentially treated with an anti-coagulant.

"Sample" relates to an aqueous suspension comprising cellular material and comprises body fluids such as lymph, cerebrospinal fluid, blood (whole blood and plasma), saliva, but also comprises e.g. the aqueous fraction of homogenized suspensions such as e.g. muscles, brain, liver, or other tissues.

"Eukaryotic" in the present invention relates to any type of eukaryotic organism, such as animals, in particular animals containing blood, and comprises invertebrate animals such as crustaceans and vertebrates. Vertebrates comprise both cold-blooded (fish, reptiles, amphibians) and warm blooded animal (birds and mammals). Mammals comprise in particular primates and more particularly humans. The term "eukaryotic" in the present invention does not comprise eukaryotic unicellular organisms such as pathogenic or opportunistic unicellular fungi and protozoa.

"Selective lysis" as used in the present invention is obtained when in a sample (such as blood) the percentage of micro-organism cells (such as bacterial cells) in that sample that remain intact is significantly higher (e.g. 2, 5, 10, 20, 50, 100, 250, 500, or 1,000 times more) than the percentage of the eukaryotic cells from the organism from which the sample is collected that remain intact.

"Micro-organism" as used in the present invention relates to bacteria (gram positive and gram negative bacteria, as well as bacterial spores) and unicellular fungi such as yeast and molds, which are present in the organism from which a sample has been collected, typically as a pathogen.

A first aspect of the present invention relates to a method for the selective lysis of eukaryotic cells, in particular animal cells, within a sample, which contains or is suspected to contain micro-organisms such as bacteria. The aim of the method is to increase the sensitivity of a test for the detection of minute amounts of micro-organisms in a sample (i.e. less than 10,000, 1,000, 100 or even less micro-organisms per ml of sample). As explained in the background of the invention, DNA from eukaryotic cells, in particular from animal cells, in a sample interferes with PCR based detection methods and this DNA, together with proteins and membranes form aggregates which increases viscosity after lysis and which has a dramatic impact on the filtration of a lysed sample. To solve this problem, the eukaryotic cells, in particular animal cells, are selectively lysed whereby a substantial part (i.e. more than 20%, 40%, 60%, 80%, 90% or even more that 95%) of the micro-organisms remains alive, or if killed by the treatment, still comprise the bacterial DNA within the cell wall. In methods as described in the present invention the above mentioned problems are addressed.

Methods as described in the present invention are applicable to any type of sample wherein the detection of DNA from micro-organisms, particularly from bacteria, is impaired by the presence of other cells comprising DNA, in particular cells from a host wherein the micro-organism is present as a pathogen.

Methods as described in the present invention are now further illustrated for embodiments wherein the presence of minute amounts of bacteria or fungi cells in a mammalian blood sample is investigated.

The blood sample can be stored as whole blood or a processed fraction such as plasma or a platelet preparation. Typically, methods as described in the present invention are performed on freshly isolated whole blood. Such samples are generally treated with e.g. heparin, EDTA or citrate to avoid coagulation.

Alternatively the method is performed on fresh blood by collecting the blood from a blood vessel such as an artery or vein directly in a tube with detergent and buffer.

Accordingly, a fresh blood sample or a preserved sample is supplemented with a buffer and an ionic surfactant. The selection of the buffer and its concentration are chosen in order to compensate the buffering capacity of the blood sample provided and to obtain a pH of about 9.0 or more, preferably a pH of about 9.5 or more, wherein pH values above 11.5 are particularly suitable for gram positive bacteria and fungi. In a particular embodiment, the buffer has a pH of 9.0 or more. In a preferred embodiment, the buffer has a pH of between about 9.5 and about 11.5, more preferably a pH between about 9.5 and about 10.5. In a particular embodiment, the pH to obtain in the solution comprising the sample is between about 9.5 and about 11.5, even more particular between about 9.5 and about 10.5. Equally the buffer is sufficiently concentrated such that at most a buffer volume of 200%, 150%, 100%, 50%, 20% or 10% of the sample volume is added to the sample to obtain the required change in pH.

Suitable buffers in the context of the present invention typically have a pKa above 9, above 9.5 or even above 10 and include borate, carbonate, CAPS, CAPSO, CHES, pyrophosphate, ethanolamine, and other commonly used buffers with an optimal buffering capacity in the above mentioned pH ranges.

Suitable surfactants are ionic surfactants, which at the one hand have a lytic effect on the eukaryotic cells, in particular animal cells, only and on the other hand have a solubilising effect on DNA and proteins. The ionic surfactant may either be an anionic surfactant or a cationic surfactant, i.e. a surfactant molecule having a positive ionic group.

Anionic surfactants have a negative ionic group, either based on a permanent anion such as sulfate, sulfonate or phosphate, or on a pH-dependent anion such as carboxylate. The anionic surfactant may be selected from the group consisting of alkyl sulfates, alkyl ether sulfates, docusates, sulfonate fluorosurfactants, alkyl benzene sulfonates, alkyl aryl ether phosphates, alkyl ether phosphates, alkyl carboxylates, and carbocxylate fluorosurfactants. Examples of anionic surfactants are ammonium lauryl sulfate, sodium dodecyl sulfate (SDS), sodium deoxycholate, sodium-n-dodecylbenzenesulfonate, sodium lauryl ether sulfate (SLES), sodium myreth sulfate, dioctyl sodium sulfosuccinate, perfluorooctanesulfonate (PFOS), perfluorobutanesulfonate, sodium stearate, sodium lauroyl sarcosinate, perfluorononanoate, and perfluorooctanate (PFOA or PFO).

Cationic surfactants comprise a positive ionic group and pH-dependent cationic surfactants are based on primary, secondary or tertiary amines, whereas permanently charged cationic surfactants are based on quaternary ammonium cation. Examples of cationic surfactants are cetyl trimethylammonium bromide (CTAB), cetyl trimethylammonium chloride (CTAC), cetylpyridinium chloride (CPC), Polyethoxylated tallow amine (POEA), benzalkonium chloride (BAC), benzthonium chloride (BZT), 5-bromo-5-nitro-1,3-dioxane, dimethyldioctadecylammonium chloride and dioctadecyldimethylammonium bromide (DODAB).

The most effective concentration of surfactant depends from surfactant to surfactant, but typically is within the range of between 0.1 and 5%, more particularly between 0.1 and 1%. Depending from the detergent (solid or liquid) % refers to respectively w/v % or v/v %.

The incubation of a blood sample in the presence of buffer and detergent is performed within 10 minutes, preferably between 30 seconds and 10 minutes and more preferably between about 1 to 3 minutes, between about 1 to 5 minutes, between about 1 to 8 minutes, or between about 1 to 10 minutes, at temperatures between 10° C. and 30° C. Methods according to the present invention have the advantage that a selective lysis is obtained within 0.5 to 3 minutes, at temperatures below 30° C. Accordingly, the methods can be generally performed at ambient temperatures without the need to heat the sample.

Optionally, after the lysis the pH of the lysed sample is brought to a neutral value (i.e. between 7 and 8) by the addition of an acid or acidic buffer. It was found that a lysed sample at neutral pH could be stored for a prolonged time (up to 1, 2, 6, 12 or even 24 hours) without further lysis of bacterial cells and without dramatic changes in the fluidic properties of the lysed sample.

Another parameter investigated in the methods of the present invention is the evaluation of the fluidic properties of the blood sample after lysis This can be determined by verifying which volume of lysed blood can be filtered through a 0.22 μm filter with a diameter of 2.5 cm. Methods in accordance with the present invention allow the filtration of at least 2, 5, 7.5 or even 10 ml of whole blood which was diluted by addition of 1 volumes of buffer/detergent solution to 1 volume of sample.

Generally, methods in accordance with the present invention comprise a step wherein the intact micro-organisms are separated from the sample, typically performed by centrifugation or filtration. In particular embodiments intact micro-organisms are separated from the sample by passage of the lysed sample through a filter, with a pore size below 1 μm, to retain micro-organisms which have typically a size between 0.5 and 10 μm, such as commercially available filters with a pore size of 0.4 or 0.22 μm. For the filtration of samples, a wide variety of commercially available devices exists, such as filters adapted to fit on a syringe such that after lysis within in syringe, the fluid can be passed over the filter by manual pressure on the plunger of the syringe. These devices may be part of the kit-of-parts of the present invention.

Hereafter the presence of micro-organisms on the filter can be investigated. In particular embodiments the presence of micro-organisms is investigated by PCR. For this purpose, the micro-organisms can be washed away from the filter and further treated for PCR amplification. Alternatively the filter is rinsed with a lysis buffer to release the DNA from the micro-organisms, which is further used in a PCR reaction.

The lysis of the sample, filtration and detection of micro-organisms can be performed within one device (schematically depicted in FIG. 1). Accordingly, one aspect of the present invention relates to a device (1), comprising a lysis chamber (2) for accepting a sample fluid with a volume between 1 and 10 ml, a reservoir (3) comprising an alkaline buffer with surfactants as described above, or a reservoir comprising an alkaline buffer (31) as described above and a reservoir comprising surfactants (32) as described above, the reservoirs connected to the lysis chamber (2). Within the device, the lysis chamber is connected to a filter (4) for filtering the sample after lysis whereby micro-organisms are retained on the filter. The device further comprises channels to remove the micro-organisms from the filter and lyse them in a separate chamber. Alternatively, the device further comprises means for lysing micro-organisms on the filter, and channels to transfer DNA from lysed bacterial or fungal cells from the filter to a separate chamber. The device can further contain a DNA purification and detection chamber (5) for assaying the presence of DNA. Typically the detection chamber is a PCR module.

Figure 2:
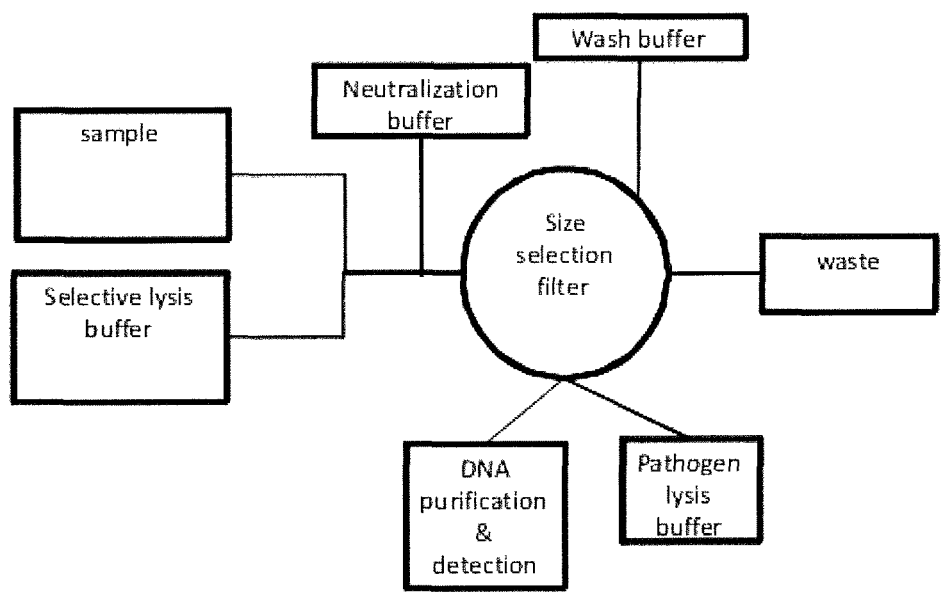
FIG. 2 shows an example of an integrated device comprising a selective lysis unit as described in embodiments of the present invention

An example of a device wherein selective lysis and subsequent DNA purification and identification takes place is depicted in FIG. 2.

Other arrangements of the systems and methods embodying the invention will be obvious for those skilled in the art.

It is to be understood that although preferred embodiments, specific constructions and configurations, as well as materials, have been discussed herein for devices according to the present invention, various changes or modifications in form and detail may be made without departing from the scope and spirit of this invention.

EXAMPLE 1

Recovery of Micro-organisms from Blood Samples

About 1.000 colony forming units (cfu) of either *Pseudomonas aeruginosa* or *Candida albicans* were spiked in each 5 ml sample of human whole blood. An equal volume of lysis buffer (500 mM Na carbonate (pH 10.0) and either 1.0% Triton X-100 (final concentration) or 1% sodium dodecyl sulfate (final concentration) was added and the mixture was incubated for 3 minutes at room temperature (about 23° C.).

After the incubation the lysed sample was neutralized with a 1 M Tris solution to restore the pH. The samples were centrifuged and washed with 1 ml phosphate-buffered saline (PBS). Hereafter the micro-organisms were lysed by adding pre-heated 200 mM NaOH, 1% SDS and their DNA was purified using standard silica spin columns after the eluates were neutralized with 1 M citric acid.

EXAMPLE 2

Detection of Microbial DNA

For elution from the filter and for alkaline lysis of the micro-organisms, the microbial cells were resuspended in 100 µl of a lysis solution containing 50 mM NaOH and 0.25% SDS. Subsequently the samples were incubated for 10 min at 70° C., cooled quickly to room temperature and neutralized by addition of 30 µl 500 mM Tris-HCl, pH 7.0 (yielding a final concentration of 150 mM Tris, i.e. 3 times the NaOH concentration).

For crude lysate PCR, unlysed cells and debris were removed from the sample by centrifugation (5 min, 14,000 g). 1 µl of supernatant was added to a 25 µl PCR reaction. Detection by PCR was based on a Taqman PCR assay targeting the rRNA gene (Apollo). The PCR reaction was conducted in Taqman Universal mastermix (Applied Biosystems), using 500 nM forward primer and 300 nM reverse primer and FAM-BHQ1 labeled probe (all oligonucleotides custom synthesized by Biolegio BV). The PCR reaction was performed in a Biorad CFX real-time PCR system. After an initial heating step of 10 min at 95° C. to activate the hot-start polymerase, 50 cycles of 15 sec at 95° C. and 1 min at 60° C. were used for amplification. Fluorescence signals were detected in each cycle during the 60° C. step. Data analysis was performed with the Biorad CFX software.

The $C_t$ (cycle threshold) is defined as the number of cycles required for the fluorescent signal to cross the threshold (i.e. exceeds background level). $C_t$ levels are inversely proportional to the amount of target nucleic acid in the sample (i.e. the lower the $C_t$ level the greater the amount of target nucleic acid in the sample). $C_t$ values <29 are strong positive reactions indicative of abundant target nucleic acid in the sample. $C_t$ values of 30-37 are positive reactions indicative of moderate amounts of target nucleic acid. $C_t$ values of 38-40 are weak reactions indicative of minimal amounts of target nucleic acid which could represent environmental contamination.

Figure 3:
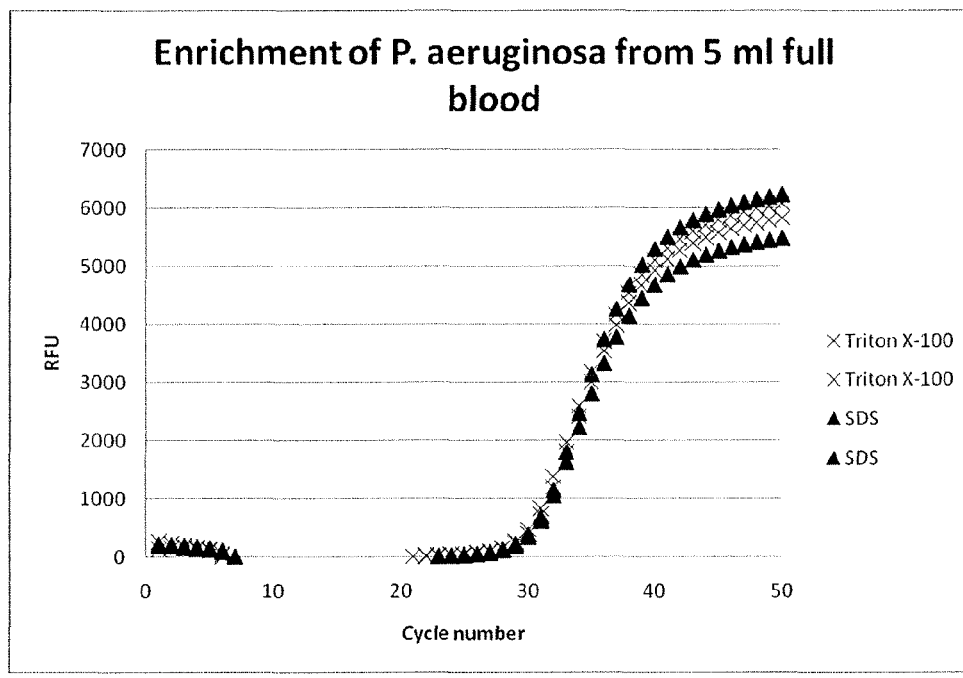
FIG. 3 shows the result of a quantitative RT-PCR for *P. aeroginosa* enriched from whole blood samples.
Figure 4:
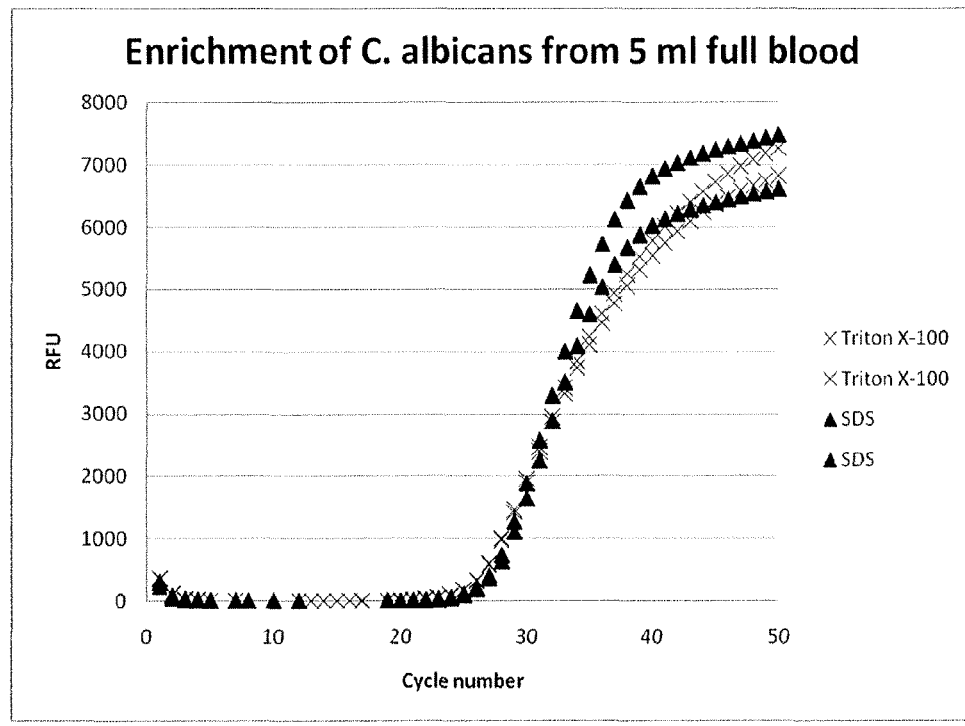
FIG. 4 shows the result of a quantitative RT-PCR for *C. albicans* enriched from whole blood samples.

FIGS. 3 and 4 illustrate the results of the Taqman PCR assay for the differential lysis and enrichment of micro-organisms from whole blood. FIG. 3 displays the relative fluorescence obtained during the PCR amplification of *P. aeruginosa* DNA from initially 1,000 cfu in 5 ml blood, wherein the lysis of the white and red blood cells were performed with either Triton X-100 or sodium dodecyl sulfate. FIG. 4 displays the relative fluorescence obtained during the PCR amplification of *C. albicans* DNA from initially 1,000 cfu in 5 ml blood, wherein the lysis of the white and red blood cells were performed with either Triton X-100 or sodium dodecyl sulfate. Both, FIG. 3 and FIG. 4 show that the non-ionic surfactant and the ionic surfactant resulted in similar fluorescence yields. Hence, it can be concluded that the ionic surfactant is as efficient in lysing blood cells and removing PCR inhibitory compounds as non-ionic surfactants. Thus, ionic surfactants are suitable for selective lysis of blood cells, and can be used in combination with high pH for differentially lysing blood cells while keeping micro-organisms that are present in the blood sample intact. Furthermore, *P. aeruginosa* is a gram negative bacterium and is very vulnerable to detergents. Yet it survives the lysis of the blood cells. *C. albicans* is a unicellular fungus, and is well known for its rigid cell walls and for being difficult to lyse. However, the method of the present invention permits detection of a small number of *C. albicans* cells within the standard volume of blood sample usually obtained from patients for routine culturing based diagnostics. Moreover, the method can be performed at ambient temperature such as room temperature, and does not require adding any enzymes for degrading and removing the nucleic acids and proteins of the eukaryotic cells.

Having described the invention, the following is claimed:

1. A method for selective lysis of blood cells within a mammalian blood sample containing or suspected to contain micro-organisms, said method comprising the steps of:
   a) providing the mammalian blood sample with the blood cells, the mammalian blood sample containing or suspected to contain micro-organisms, wherein:
      said mammalian blood sample has a volume between 1 ml and 20 ml,
      said micro-organisms are selected from the group consisting of bacteria and unicellular fungi, and
      there are less than 10,000 micro-organisms per milliliter of the mammalian blood sample;
   b) adding an ionic surfactant and a buffer to said mammalian blood sample to obtain a solution with a pH of between about 9.0 and about 11.5, wherein the ionic surfactant is present in a concentration of 0.1% to 5% (w/v % or v/v %) in the solution; and
   c) incubating the solution for a time period sufficiently long to selectively lyse the blood cells within the mammalian blood sample, while keeping the micro-organisms intact, wherein the percentage of micro-organism cells that remain intact in the mammalian blood sample is at least two times higher than the percentage of blood cells that remain intact in the mammalian blood sample.

2. The method according to claim 1, wherein said incubating step c) is performed within a time period of between 30 seconds and 10 minutes.

3. The method according to claim 1, wherein the ratio between the volume of added ionic surfactant and added buffer and the volume of the mammalian blood sample is between 2/1 and 1/10.

4. The method according to claim 1, wherein the ionic surfactant is selected from the group consisting of anionic surfactants and cationic surfactants,
   wherein the anionic surfactant is selected from the group consisting of alkyl sulfates, alkyl ether sulfates, docusates, sulfonate fluorosurfactants, alkyl benzene sulfonates, alkyl aryl ether phosphates, alkyl ether phosphates, alkyl carboxylates, and carbocxylate fluorosurfactants, more preferably selected from the group consisting of ammonium lauryl sulfate, sodium dodecyl sulfate (SDS), sodium deoxycholate, sodium-n-dodecylbenzenesulfonate, sodium lauryl ether sulfate (SLES), sodium myreth sulfate, dioctyl sodium sulfosuccinate, perfluorooctanesulfonate (PFOS), perfluorobutanesulfonate, sodium stearate, sodium lauroyl sarcosinate, perfluorononanoate, and perfluorooctanate (PFOA or PFO), and
   wherein the cationic surfactant is selected from the group consisting of cetyl trimethylammonium bromide (CTAB), cetyl trimethylammonium chloride (CTAC), cetylpyridinium chloride (CPC), Polyethoxylated tallow amine (POEA), benzalkonium chloride (BAC), benzthonium chloride (BZT), 5-bromo-5-nitro-1,3-dioxane, dimethyldioctadecylammonium chloride and dioctadecyldimethylammonium bromide (DODAB).

5. The method according to claim 1, wherein the ionic surfactant is sodium dodecyl sulfate (SDS).

6. The method according to claim 1, further comprising the step of centrifuging said incubated solution and isolating the intact micro-organisms.

7. The method according to claim 1, further comprising the step of filtering said incubated solution on a filter with a pore size which retains the intact micro-organisms on said filter.

8. The method according to claim 1, further comprising the step of lysing said intact micro-organisms of step c) using a lysis buffer to release DNA from the micro-organisms.

9. The method according to claim 1, further comprising a nucleic acid based molecular assay.

10. The method according to claim 1, wherein said incubating step c) is perfoiined at a temperature between 10° C. and 30° C.

* * * * *